(12) United States Patent
Ortiz et al.

(10) Patent No.: US 7,879,070 B2
(45) Date of Patent: *Feb. 1, 2011

(54) ELECTROACTIVE POLYMER-BASED ACTUATION MECHANISM FOR GRASPER

(75) Inventors: Mark Ortiz, Milford, OH (US); Frederick Shelton, IV, Hillsboro, OH (US); Jeffrey Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 955 days.

This patent is subject to a terminal disclaimer.

(21) Appl. No.: 11/162,992

(22) Filed: Sep. 30, 2005

(65) Prior Publication Data

US 2006/0047303 A1 Mar. 2, 2006

Related U.S. Application Data

(63) Continuation-in-part of application No. 11/082,495, filed on Mar. 17, 2005, now Pat. No. 7,506,790.

(60) Provisional application No. 60/591,694, filed on Jul. 28, 2004.

(51) Int. Cl.
*A61B 17/00* (2006.01)
(52) U.S. Cl. ............... 606/205; 227/19; 227/175.1; 227/176.1; 227/180.1
(58) Field of Classification Search .......... 606/205–207
See application file for complete search history.

(56) References Cited

U.S. PATENT DOCUMENTS

| | | | |
|---|---|---|---|
| 2,711,461 A | 6/1955 | Happe | |
| 4,473,077 A | 9/1984 | Noiles et al. | |
| 4,543,090 A | 9/1985 | McCoy | |
| 4,554,064 A | 11/1985 | McClintock et al. | |
| 4,566,620 A | 1/1986 | Green et al. | |
| 4,601,705 A | 7/1986 | McCoy | |
| 4,753,223 A | 6/1988 | Bremer | |
| 4,892,545 A | 1/1990 | Day et al. | |
| 5,031,814 A | 7/1991 | Tompkins et al. | |
| 5,040,715 A | 8/1991 | Green et al. | |
| 5,071,052 A | 12/1991 | Rodak et al. | |

(Continued)

FOREIGN PATENT DOCUMENTS

DE 4015562 A1 11/1991

(Continued)

OTHER PUBLICATIONS

Dec. 5, 2008 Office Action for U.S. Appl. No. 11/162,991.

(Continued)

*Primary Examiner*—Todd E Manahan
*Assistant Examiner*—Michael G Mendoza

(57) ABSTRACT

Methods and devices are provided for actuating and/or articulating a grasping device. In one exemplary embodiment, a grasping device is provided having a shaft with an end effector having opposed jaws coupled to the shaft. An electrically expandable and contractible actuator, such as an electroactive polymer actuator, can be used to actuate the end effector to open and close the opposed jaws to grasp tissue or other objects. In another embodiment, an electroactive polymer actuator can be used to pivotally or angularly adjust a position of the end effector relative to the shaft by delivering energy to the electroactive polymer actuator.

24 Claims, 14 Drawing Sheets

U.S. PATENT DOCUMENTS

| | | |
|---|---|---|
| 5,137,198 A | 8/1992 | Nobis et al. |
| 5,171,249 A | 12/1992 | Stefanchik et al. |
| 5,202,914 A | 4/1993 | Kim et al. |
| 5,263,629 A | 11/1993 | Trumbull et al. |
| 5,290,240 A | 3/1994 | Horres, Jr. |
| 5,312,023 A | 5/1994 | Green et al. |
| 5,330,087 A | 7/1994 | Murray et al. |
| 5,372,124 A | 12/1994 | Takayama et al. |
| 5,387,194 A | 2/1995 | Williams et al. |
| 5,389,098 A | 2/1995 | Tsuruta et al. |
| 5,397,046 A | 3/1995 | Savage et al. |
| 5,397,324 A | 3/1995 | Carroll et al. |
| 5,399,256 A | 3/1995 | Bohs et al. |
| 5,403,312 A | 4/1995 | Yates et al. |
| 5,413,267 A | 5/1995 | Solyntjes et al. |
| 5,413,268 A | 5/1995 | Green et al. |
| 5,431,668 A | 7/1995 | Burbank, III et al. |
| 5,441,193 A | 8/1995 | Gravener |
| 5,445,304 A | 8/1995 | Plyley et al. |
| 5,465,895 A | 11/1995 | Knodel et al. |
| 5,468,250 A * | 11/1995 | Paraschac et al. ........... 606/205 |
| 5,484,095 A | 1/1996 | Green et al. |
| 5,503,638 A | 4/1996 | Cooper et al. |
| 5,520,787 A | 5/1996 | Hanagan et al. |
| 5,535,937 A | 7/1996 | Boiarski et al. |
| 5,542,594 A | 8/1996 | McKean et al. |
| 5,549,628 A | 8/1996 | Cooper et al. |
| 5,555,555 A | 9/1996 | Sato et al. |
| 5,562,239 A | 10/1996 | Boiarski et al. |
| 5,584,425 A | 12/1996 | Savage et al. |
| 5,592,668 A | 1/1997 | Harding et al. |
| 5,599,329 A | 2/1997 | Gabbay |
| 5,601,582 A | 2/1997 | Shelton et al. |
| 5,609,285 A | 3/1997 | Grant et al. |
| 5,624,452 A | 4/1997 | Yates |
| 5,634,584 A | 6/1997 | Okorocha et al. |
| 5,653,721 A | 8/1997 | Knodel et al. |
| 5,661,887 A | 9/1997 | Byrne et al. |
| 5,665,285 A | 9/1997 | Hattori et al. |
| 5,667,517 A | 9/1997 | Hooven |
| 5,669,918 A | 9/1997 | Balazs et al. |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,693,042 A | 12/1997 | Boiarski et al. |
| 5,702,409 A | 12/1997 | Rayburn et al. |
| 5,704,534 A | 1/1998 | Huitema et al. |
| 5,709,334 A | 1/1998 | Sorrentino et al. |
| 5,735,445 A | 4/1998 | Vidal et al. |
| 5,769,892 A | 6/1998 | Kingwell |
| 5,779,130 A | 7/1998 | Alesi et al. |
| 5,792,165 A | 8/1998 | Klieman et al. |
| 5,797,537 A | 8/1998 | Oberlin et al. |
| 5,810,855 A | 9/1998 | Rayburn et al. |
| 5,826,776 A | 10/1998 | Schulze et al. |
| 5,829,662 A | 11/1998 | Allen et al. |
| 5,855,565 A | 1/1999 | Bar-Cohen et al. |
| 5,865,361 A | 2/1999 | Milliman et al. |
| 5,868,744 A | 2/1999 | Willmen |
| 5,876,401 A | 3/1999 | Schulze et al. |
| 5,901,895 A | 5/1999 | Heaton et al. |
| 5,902,312 A | 5/1999 | Frater et al. |
| 5,908,427 A | 6/1999 | McKean et al. |
| 5,918,791 A | 7/1999 | Sorrentino et al. |
| 5,959,852 A | 9/1999 | Deloy et al. |
| 5,964,774 A | 10/1999 | McKean et al. |
| 5,972,165 A | 10/1999 | Sethna et al. |
| 6,010,054 A | 1/2000 | Johnson et al. |
| 6,032,849 A | 3/2000 | Mastri et al. |
| 6,033,427 A | 3/2000 | Lee |
| 6,063,097 A | 5/2000 | Oi et al. |
| 6,079,606 A | 6/2000 | Milliman et al. |
| 6,109,500 A | 8/2000 | Alli et al. |
| 6,202,914 B1 | 3/2001 | Geiste et al. |
| 6,241,139 B1 | 6/2001 | Milliman et al. |
| 6,302,311 B1 | 10/2001 | Adams et al. |
| 6,330,965 B1 | 12/2001 | Milliman et al. |
| 6,488,197 B1 | 12/2002 | Whitman |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,514,237 B1 | 2/2003 | Maseda |
| 6,545,384 B1 | 4/2003 | Pelrine et al. |
| 6,577,899 B2 | 6/2003 | Lebel et al. |
| 6,583,533 B2 | 6/2003 | Pelrine et al. |
| 6,586,859 B2 | 7/2003 | Kornbluh et al. |
| 6,595,852 B2 | 7/2003 | Wang |
| 6,652,521 B2 | 11/2003 | Schulze |
| 6,656,193 B2 | 12/2003 | Grant et al. |
| 6,667,825 B2 | 12/2003 | Lu et al. |
| 6,669,073 B2 | 12/2003 | Milliman et al. |
| 6,699,245 B2 | 3/2004 | Dinger et al. |
| 6,716,233 B1 | 4/2004 | Whitman |
| 6,740,079 B1 | 5/2004 | Eggers et al. |
| 6,770,027 B2 | 8/2004 | Banik et al. |
| 6,786,382 B1 | 9/2004 | Hoffman |
| 6,830,174 B2 | 12/2004 | Hillstead et al. |
| 6,835,173 B2 | 12/2004 | Couvillon, Jr. |
| 6,840,246 B2 | 1/2005 | Downing |
| 6,905,057 B2 | 6/2005 | Swayze et al. |
| 6,913,579 B2 | 7/2005 | Truckai et al. |
| 6,923,804 B2 | 8/2005 | Eggers et al. |
| 6,959,852 B2 | 11/2005 | Shelton, IV et al. |
| 6,964,363 B2 | 11/2005 | Wales et al. |
| 6,969,395 B2 | 11/2005 | Eskuri |
| 6,978,921 B2 | 12/2005 | Shelton, IV et al. |
| 6,981,628 B2 | 1/2006 | Wales |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,063,699 B2 | 6/2006 | Hess et al. |
| 7,074,217 B2 | 7/2006 | Strul et al. |
| 7,083,075 B2 | 8/2006 | Swayze et al. |
| 7,111,769 B2 | 9/2006 | Wales et al. |
| 7,140,528 B2 | 11/2006 | Shelton, IV |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,208,005 B2 | 4/2007 | Frecker et al. |
| 7,213,736 B2 | 5/2007 | Wales et al. |
| 7,238,195 B2 | 7/2007 | Viola |
| 7,320,700 B2 | 1/2008 | Cooper et al. |
| 7,338,509 B2 | 3/2008 | Mattison |
| 7,354,447 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,509 B2 | 7/2008 | Ortiz et al. |
| 7,407,074 B2 | 8/2008 | Ortiz et al. |
| 7,431,730 B2 | 10/2008 | Viola |
| 7,487,899 B2 | 2/2009 | Shelton, IV et al. |
| 7,506,790 B2 | 3/2009 | Shelton, IV |
| 7,513,408 B2 | 4/2009 | Shelton, IV et al. |
| 7,517,356 B2 | 4/2009 | Heinrich |
| 7,559,452 B2 | 7/2009 | Wales et al. |
| 7,607,557 B2 | 10/2009 | Shelton, IV et al. |
| 7,641,093 B2 | 1/2010 | Doll et al. |
| 2001/0029384 A1 | 10/2001 | Nicholas et al. |
| 2002/0074005 A1 | 6/2002 | Hogg et al. |

| | | | |
|---|---|---|---|
| 2002/0108112 A1 | 8/2002 | Wallace et al. | |
| 2002/0165541 A1 | 11/2002 | Whitman | |
| 2003/0065358 A1 | 4/2003 | Frecker et al. | |
| 2003/0069474 A1 | 4/2003 | Couvillon | |
| 2003/0199870 A1 | 10/2003 | Truckai et al. | |
| 2003/0207606 A1 | 11/2003 | Ho | |
| 2003/0236531 A1 | 12/2003 | Couvillon | |
| 2004/0002726 A1 | 1/2004 | Nunez et al. | |
| 2004/0050971 A1 | 3/2004 | Rueger et al. | |
| 2004/0054322 A1 | 3/2004 | Vargas | |
| 2004/0068224 A1 | 4/2004 | Couvillon et al. | |
| 2004/0097971 A1 | 5/2004 | Hughett | |
| 2004/0138700 A1 | 7/2004 | Cooper et al. | |
| 2004/0149802 A1 | 8/2004 | Whitman | |
| 2004/0232195 A1 | 11/2004 | Shelton et al. | |
| 2004/0232196 A1 | 11/2004 | Shelton et al. | |
| 2004/0232197 A1 | 11/2004 | Shelton et al. | |
| 2005/0006429 A1 | 1/2005 | Wales et al. | |
| 2005/0006431 A1 | 1/2005 | Shelton et al. | |
| 2005/0006434 A1 | 1/2005 | Wales et al. | |
| 2005/0067457 A1 | 3/2005 | Shelton et al. | |
| 2005/0067458 A1 | 3/2005 | Swayze et al. | |
| 2005/0085693 A1 | 4/2005 | Belson et al. | |
| 2005/0102017 A1 | 5/2005 | Mattison | |
| 2005/0165415 A1 | 7/2005 | Wales | |
| 2005/0173490 A1 | 8/2005 | Shelton | |
| 2006/0016853 A1 | 1/2006 | Racenet | |
| 2006/0022014 A1 | 2/2006 | Shelton et al. | |
| 2006/0022015 A1 | 2/2006 | Shelton et al. | |
| 2006/0025810 A1 | 2/2006 | Shelton | |
| 2006/0025811 A1 | 2/2006 | Shelton | |
| 2006/0025812 A1 | 2/2006 | Shelton | |
| 2006/0025813 A1 | 2/2006 | Shelton et al. | |
| 2006/0025816 A1 | 2/2006 | Shelton | |
| 2006/0060630 A1 | 3/2006 | Shelton et al. | |
| 2006/0180634 A1 | 8/2006 | Shelton et al. | |
| 2006/0190028 A1 | 8/2006 | Wales et al. | |
| 2007/0084897 A1 | 4/2007 | Shelton et al. | |
| 2007/0102453 A1 | 5/2007 | Morgan et al. | |
| 2007/0170225 A1 | 7/2007 | Shelton et al. | |
| 2010/0181364 A1 | 7/2010 | Shelton, IV et al. | |

FOREIGN PATENT DOCUMENTS

| | | |
|---|---|---|
| DE | 4303544 A1 | 9/1993 |
| DE | 19534320 C1 | 2/1997 |
| DE | 196 47 354 A1 | 5/1998 |
| EP | 201883 A2 | 11/1986 |
| EP | 0500353 A1 | 8/1992 |
| EP | 0674876 | 4/1995 |
| EP | 0741966 A2 | 11/1996 |
| EP | 741996 A2 | 11/1996 |
| EP | 0 832 605 A | 4/1998 |
| EP | 0832605 A1 | 4/1998 |
| EP | 1 323 384 A | 7/2003 |
| EP | 1 522 264 A | 4/2005 |
| EP | 1522264 A1 | 4/2005 |
| EP | 1621137 | 2/2006 |
| EP | 1621141 | 2/2006 |
| EP | 1621143 A2 | 2/2006 |
| EP | 1621151 A2 | 2/2006 |
| EP | 1693008 A1 | 8/2006 |
| NL | DE19537299 | 4/1997 |
| NL | DE19643073 | 4/1997 |
| NL | DE19647354 | 5/1998 |
| NL | DE1993372 | 2/2001 |
| WO | WO 99/02090 | 1/1999 |
| WO | WO-0078222 A1 | 12/2000 |
| WO | WO-0156455 | 8/2001 |
| WO | WO-0162158 A2 | 8/2001 |
| WO | WO-0162163 A1 | 8/2001 |
| WO | WO-0228268 | 4/2002 |
| WO | 03088845 A2 | 10/2003 |
| WO | 03090630 A2 | 11/2003 |
| WO | 03094746 A1 | 11/2003 |
| WO | WO 03/094743 | 11/2003 |
| WO | WO-03094743 A1 | 11/2003 |
| WO | WO-2004014238 A2 | 2/2004 |
| WO | WO 2004/050971 | 6/2004 |
| WO | WO-2004050971 A2 | 6/2004 |
| WO | 2004086987 A1 | 10/2004 |

OTHER PUBLICATIONS

Dec. 12, 2008 Office Action for U.S. Appl. No. 11/162,984.
U.S. Appl. No. 11/082,495, filed Mar. 17, 2005, Shelton, IV.
European Search Report for 05254681.9, dated May 15, 2009. (3 pages).
European Search Report for 05254700.7, dated May 15, 2009. (3 pages).
European Search Report for 05254699.1, dated May 15, 2009. (3 pages).
Chinese Office Action for Application No. 200610146378.8 dated Jul. 24, 2009.
Chinese Office Action for Application No. 200610144755.4 dated Aug. 7, 2009.
Dec. 8, 2008, Office Action for U.S. Appl. No. 11/162,992.
Mar. 10, 2009, Office Action for Mexican Application No. PA/A/2005/008045.
International Search Report for EP App. No. 06255053.8, Jan. 25, 2007.
International Search Report for EP App. No. 05254694.2, Jan. 12, 2006.
International Search Report for EP App. No. 05254685.0, Jan. 12, 2006.
International Search Report for EP App. No. 05254695.9, Jan. 12, 2006.
International Search Report for EP App. No. 05254680.1, Jan. 12, 2006.
Communication for 06 255 058.7.
EPO Search Report dated Feb. 26, 2008 for Application No. 05254700.7.
EPO Search Report dated Feb. 29, 2008 for Application No. 05254681.9.
EPO Search Report dated Mar. 25, 2008 for Application No. 05254703.1.
EPO Search Report dated Mar. 3, 2008 for Application No. 05254699.1.
European Search Report for EP #05254684.3, dated Mar. 27, 2008.
European Search Report for EP 06255057.9, dated Oct. 19, 2007.
European Search Report for EPO Application No. 06255053, dated Jan. 25, 2007.
European Search Report for EPO Application No. 06255057, dated Jan. 29, 2007.
European Search Report for EPO Application No. 06255058, dated Jan. 31, 2007.
European Search Report for EPO Application No. 06255062, dated Nov. 23, 2006.
European Search Report for EPO Application No. 06255064, dated Feb. 9, 2007.
European Search Report for EPO Application No. 06255065, dated Feb. 15, 2007.
Guidelines for Hand and Power Tools' http://www.osha.gov/doc/outreachtraining/htmlfiles/tools.html, OSHA, May 1996, p. 3.

* cited by examiner

ELECTROACTIVE POLYMER-BASED
ACTUATION MECHANISM FOR GRASPER

CROSS REFERENCE TO RELATED
APPLICATIONS

This application is a continuation-in-part of U.S. patent application Ser. No. 11/082,495 filed on Mar. 17, 2005, now U.S. Pat. No. 7,506,790, and entitled "Surgical Instrument Incorporating an Electrically Actuated Articulation Mechanism," which claims priority to U.S. Provisional Application No. 60/591,694 filed on Jul. 28, 2004 and entitled "Surgical Instrument Incorporating an Electrically Actuated Articulation Mechanism." These applications are hereby incorporated by reference in their entireties.

FIELD OF THE INVENTION

The present invention relates broadly to surgical devices, and in particular to methods and devices for articulating and/or actuating a grasping device.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical graspers include an end effector that can be actuated to grasp tissue or other devices or objects. The end effector includes a pair of cooperating jaw members that, if the instrument is intended for endoscopic or laparoscopic applications, are capable of passing through a cannula passageway. The jaws can then be opened and closed to grasp and manipulate tissue. Some devices have end effectors that can be pivotally coupled to the shaft or a shaft that can be flexible relative to the end effector to allow the end effector to be angularly oriented to facilitate grasping of tissue. One drawback to such articulating devices, however, is that a mechanical linkage is used to transfer a force from a handle of the device to the end effector to activate the end effector. The mechanical linkage can interfere with the pivoted or curved orientation of the shaft, potentially causing it to straighten.

Accordingly, there remains a need for methods and devices for actuating and/or articulating a surgical grasper.

BRIEF SUMMARY OF THE INVENTION

The present invention generally provides methods and devices for articulating and/or actuating a laparoscopic or endoscopic grasping device. In one exemplary embodiment, the grasping device can include a shaft with an end effector formed on a distal end thereof and having opposed first and second jaws for grasping tissue or other objects. The end effector can include one or more electroactive polymer actuators coupled thereto and effective to move the jaws between an open and closed position. The device can also include a handle formed on a proximal end of the shaft with a control mechanism that is adapted to selectively deliver energy to the electroactive polymer actuator(s).

In one embodiment, each jaw can include a proximal end and a distal end, and the first and second jaws can be coupled to one another at a pivot point formed between the proximal and distal ends. One or more electroactive polymers can be coupled to the proximal end of each jaw to open or close the jaws. In one embodiment, a first electroactive polymer actuator can extend between the proximal end of the first jaw and the shaft, and a second electroactive polymer actuator can extend between the proximal end of the second jaw and the shaft. The first and second electroactive polymer actuators can be adapted to axially contract when energy is delivered thereto to pull the proximal ends of the first and second jaws toward the shaft, thereby moving the first and second jaws to an open or closed position, depending upon the configuration of the jaws. In another embodiment, an electroactive polymer actuator can extend between a proximal end of each of the first and second jaws, and it can be effective to move the first and second jaws to an open or closed position when energy is delivered to the electroactive polymer actuator(s). The device can also include a biasing element, such as a spring, that is adapted to bias the jaws to an open or closed position.

A method for grasping objects is also provided and can include inserting a grasping device into a lumen of a body, and delivering energy to at least one electroactive polymer actuator coupled to at least one of the first and second jaws to engage an object between the jaws. In one exemplary embodiment, the jaws can be biased to an open position and the electroactive polymer actuator can close the jaws when energy is delivered thereto. In another embodiment, the jaws can be biased to a closed position, and the electroactive polymer actuator can open the jaws when energy is delivered thereto.

In another embodiment, a grasping device is provided having a shaft, and an end effector movably coupled to the shaft by an articulation joint. The end effector can have opposed first and second jaws formed on a distal end thereof and movable between an open and closed position. The device can also include an electroactive polymer actuator coupled to the articulation joint and adapted to move the end effector about the articulation joint relative to the shaft when energy is delivered to the electroactive polymer actuator.

While various techniques can be used to move the articulation joint using the end effector, in one embodiment the elongate shaft can include a slide bar extending therethrough and having a distal end coupled to the articulation joint. The electroactive polymer actuator can be configured to move the slide bar laterally to effect movement of the end effector. For example, the electroactive polymer actuator can include first and second electroactive polymer actuators disposed on opposed sides of the slide bar. The slide bar can include gears formed on a distal end thereof and adapted to engage corresponding gears formed in the articulation joint. In another embodiment, the articulation joint can be in the form of a pivot joint, and the electroactive polymer actuator can include a first electroactive polymer actuator extending between a first side of the end effector and a first side of the elongate shaft, and a second electroactive polymer actuator extending between a second opposed side of the end effector and a second opposed side of the elongate shaft. In yet another embodiment, the articulation joint can be in the form of a flexible portion formed between the elongate shaft and the end effector. The electroactive polymer actuator can include a plurality of electroactive polymer actuators coupled to the flexible portion at distinct locations, each of the plurality of electroactive polymer actuators being configured to change orientations when energy is selectively delivered thereto to flex the flexible portion.

Methods for grasping tissue are also provided and in one exemplary embodiment the method can include inserting an elongate shaft of a grasping device into a body lumen to position opposed jaws of an end effector movably coupled to a distal end of the elongate shaft adjacent to tissue to be grasped, delivering energy to an electroactive polymer actuator to angularly position the end effector relative to the elongate shaft and thereby position the tissue to be grasped between the opposed jaws, and closing the opposed jaws to grasp the tissue. Delivering energy to the electroactive polymer actuator can cause the electroactive polymer actuator to radially expand to move a slide bar, extending through the elongate shaft and coupled to an articulation joint formed between the elongate shaft and the end effector, laterally and thereby effect pivotal movement of the end effector. Alternatively, delivering energy to the electroactive polymer actuator can cause the electroactive polymer actuator to axially contract move a slide bar, extending through the elongate shaft and coupled to an articulation joint formed between the elongate shaft and the end effector, laterally and thereby effect pivotal movement of the end effector. In other embodiments, energy can be delivered to a first electroactive polymer actuator to move the end effector in a first direction, and to a second electroactive polymer actuator to move the end effector in a second, opposed direction. The amount of energy delivered to the electroactive polymer actuator can correspond to a degree of movement of the end effector. In yet another embodiment, delivering energy to an electroactive polymer actuator can angularly position the end effector relative to the elongate shaft by flexing a flexible portion extending between the elongate shaft and the end effector. In another embodiment, the opposed jaws can be closed by delivering energy to an electroactive polymer actuator coupled to the opposed jaws to move the opposed jaws from an open position to a closed position.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
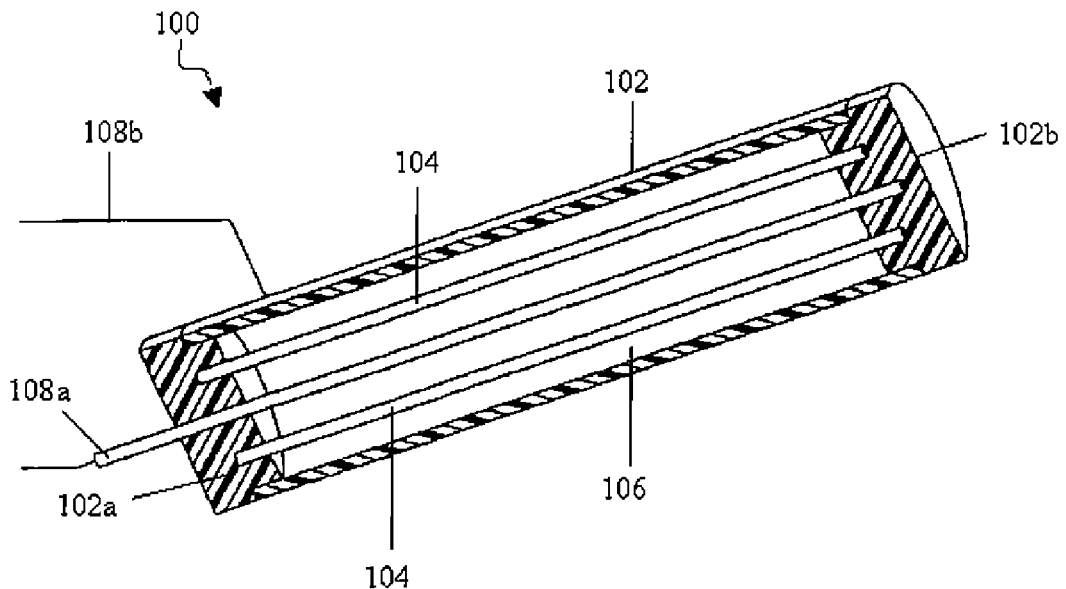
FIG. 1A is a cross-sectional view of a prior art fiber bundle type EAP actuator.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for effecting movement of one or more components of a grasping device. In one exemplary embodiment, the grasping device can include a shaft with an end effector coupled thereto and having opposed jaws that are adapted to engage tissue or other objects therebetween. An electrically expandable and contractible actuator, such as an electroactive polymer actuator, can be used to actuate the end effector, i.e., to move the jaws between an open and closed position. The end effector can also, in other embodiments, be movably coupled to a distal end of a shaft such that the end effector can be angularly oriented relative to the shaft. An electrically expandable and contractible motor, such as an electroactive polymer actuator, can be used to angularly adjust a position of the end effector relative to the shaft by delivering energy to the electroactive polymer actuator. A person skilled in the art will appreciate that the grasping device can have a variety of configurations, and that the electroactive polymer actuators disclosed herein can be incorporated into virtually any grasping device known in the art to effect actuation and/or articulation of an end effector. Moreover, the term "grasping device" is intended to include any device that has opposed pivoting jaws that come together to grasp, clamp, cut, dissect, etc. Other exemplary "grasping devices" include, by way of non-limiting example, surgical scissors, clamps, and dissector devices.

Electroactive Polymers

Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect that is caused when voltage is applied.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long stands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. The fibers can alternatively be configured to expand or lengthen. An example of a commercially available fiber EAP material is manufactured by Santa Fe Science and Technology and sold as PANION™ fiber and described in U.S. Pat. No. 6,667,825, which is hereby incorporated by reference in its entirety.

Figure 1B:
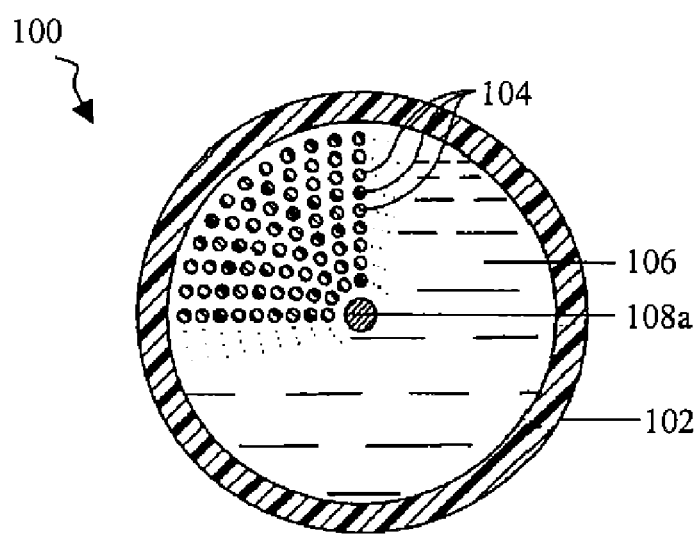
FIG. 1B is a radial cross-sectional view of the prior art actuator shown in FIG. 1A.

FIGS. 1A-1B illustrate one exemplary embodiment of an EAP actuator 100 formed from a fiber bundle. As shown, the actuator 100 generally includes a flexible conductive outer sheath 102 that is in the form of an elongate cylindrical member having opposed end caps 102a, 102b formed thereon. The outer sheath 102 can, however, have a variety of other shapes and sizes depending on the intended use. As is further shown, the outer sheath 102 is coupled to an energy delivering electrode 108a and a return electrode 108b. In the illustrated embodiment, the energy delivering electrode 108a extends through one of the end caps, e.g., end cap 102a, through the inner lumen of the conductive outer sheath 102, and into the opposed end cap, e.g., end cap 102b. The energy delivering electrode 108a can be, for example, a platinum cathode wire, and it can be coupled to any portion of the outer sheath 102. The conductive outer sheath 102 can also include an ionic fluid or gel 106 disposed therein for transferring energy from the energy delivering electrode 108a to the EAP fibers 104, which are disposed within the outer sheath 102. In particular, several EAP fibers 104 are arranged in parallel and extend between and into each end cap 102a, 102b. As noted above, the fibers 104 can be arranged in various orientations to provide a desired outcome, e.g., radial expansion or contraction, or bending movement. In use, energy can be delivered to the actuator 100 through the active energy delivering electrode 106a. The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 102b will be pulled toward one another, thereby contracting and decreasing the length of the flexible outer sheath 102.

The other type of EAP is a laminate structure, which consists of one or more layers of an EAP, a layer of ionic gel or fluid disposed between each layer of EAP, and one or more flexible plates attached to the structure. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 2A:
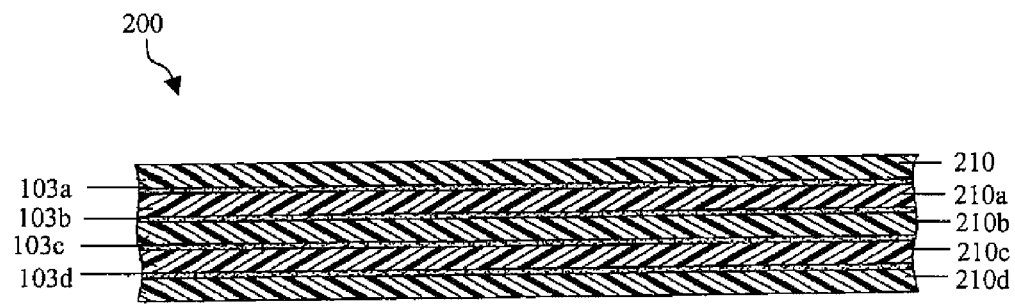
FIG. 2A is a cross-sectional view of a prior art laminate type EAP actuator having multiple EAP composite layers.
Figure 2B:
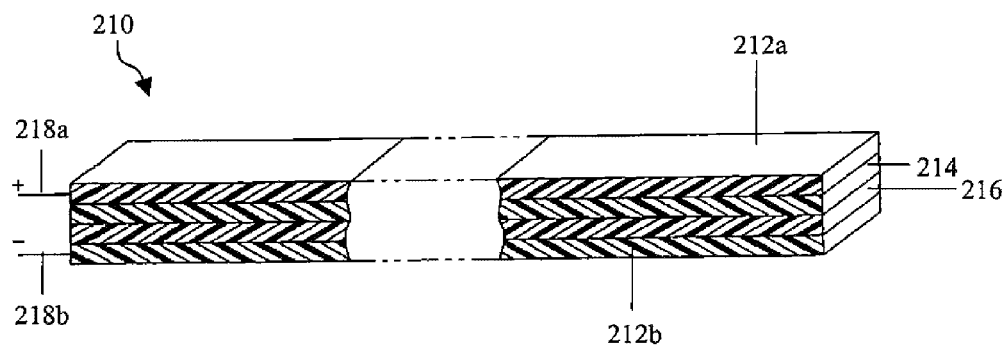
FIG. 2B is a perspective view of one of the composite layers of the prior art actuator shown in FIG. 2A.

FIGS. 2A-2B illustrate an exemplary configuration of an EAP actuator 200 formed from a laminate. Referring first to FIG. 2A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 2B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 2B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Grasping Device

Figure 3:
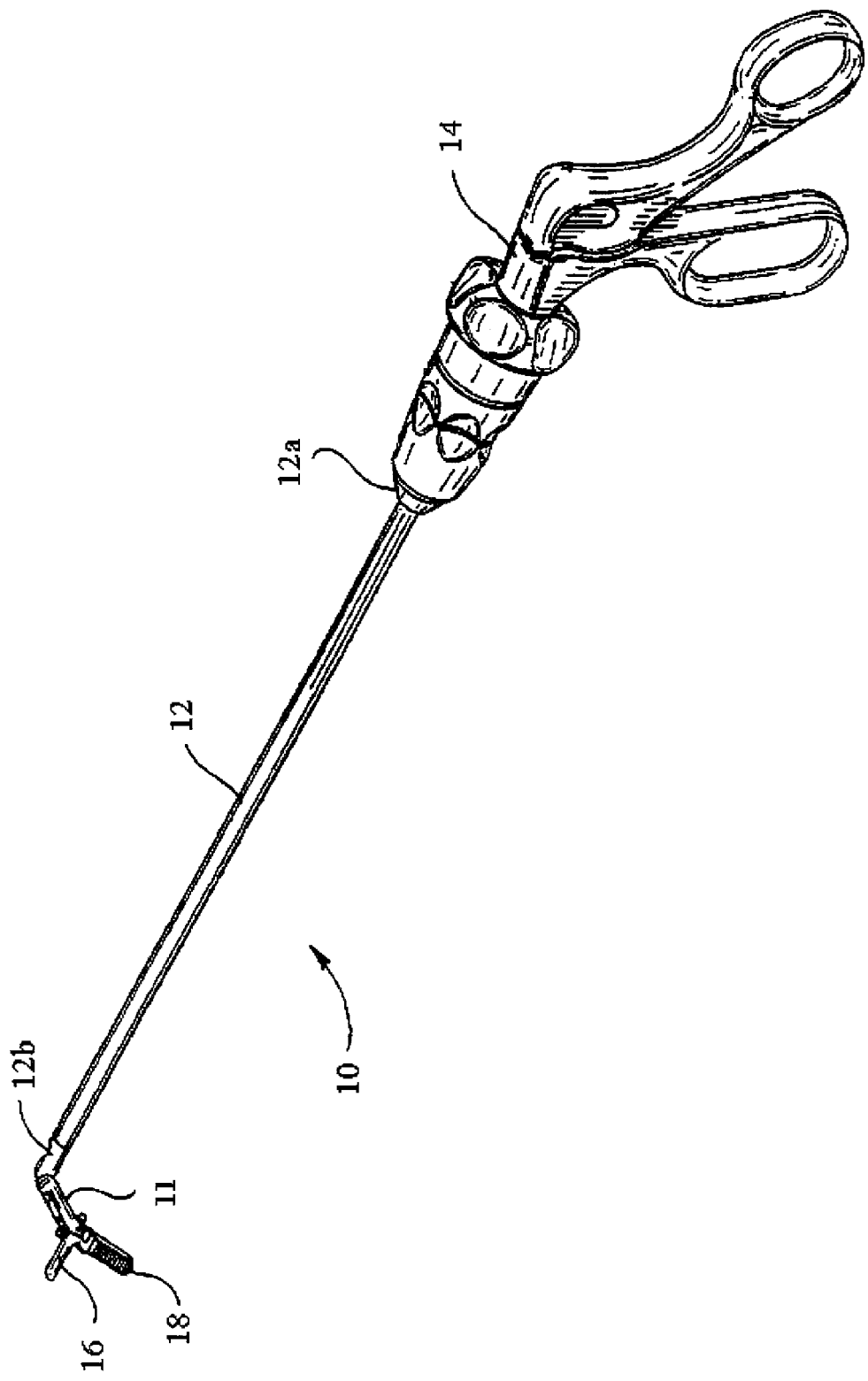
FIG. 3 is a perspective view of one exemplary embodiment of a grasping device having a handle, a shaft, and an end effector coupled to a distal end of the shaft.

As previously indicated, in an exemplary embodiment surgical grasping methods and devices are provided that utilize electrically expandable and contractible actuators, such as EAP actuators, to effect articulation and/or actuation of various components of the device. The various methods and devices disclosed herein for effecting articulation and actuation can be incorporated into virtually any grasping device known in the art, and the grasping device can include a variety of other features known in the art and not disclosed herein. FIG. 3 illustrates one exemplary embodiment of a grasping device 10 that can include one or more EAP actuators for effecting articulation and/or actuation. A person skilled in the art will appreciate that, while the various embodiments are described as having EAP actuators for affecting articulation and/or actuation without mechanical assistance, the actuators can alternatively be configured to supplement mechanical articulation and/or actuation.

In general, as shown in FIG. 3, the grasping device 10 includes a shaft 12 having a handle housing 14 coupled to a proximal end 12a thereof, and an end effector 11 coupled to the distal end 12b thereof. The end effector 11 includes opposed first and second jaws 16, 18 having teeth formed thereon and at least one EAP actuator for moving the jaws 16, 18 to grasp tissue or other objects therebetween. The handle housing 14 can include a trigger, such as a pivoting handle, rotatable knob, button, switch, sliding lever, or other mechanism formed thereon for actuating electrical energy delivery to the EAP actuator(s). In use, an object, such as tissue, is positioned between the first and second jaws 16, 18, and the first and second jaws 16, 18 are moved from an open position to a closed position to engage the object. The end effector 11 can also optionally be pivoted relative to the shaft 12 to facilitate positioning of the object therein. The grasping device 10 is particularly suitable for endoscopic and laparoscopic procedures, as the relatively small diameter of the shaft 12 allows it to fit through small access ports or pathways. The grasping device, however, can be adapted for use in a variety of medical procedures.

Actuation

Figure 4A:
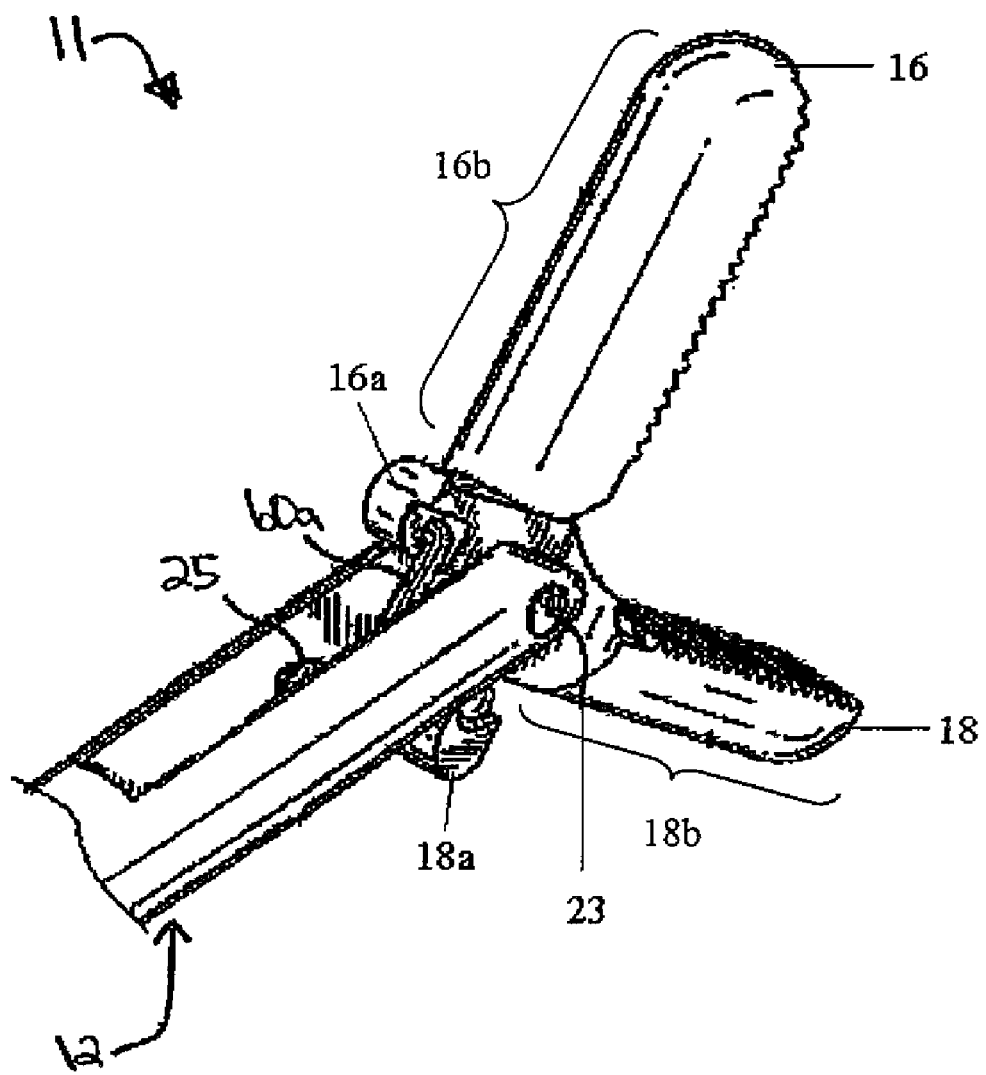
FIG. 4A is a perspective view of the end effector of FIG. 3, showing EAP actuators for effecting actuation of the end effector.

As indicated above, one or more EAP actuators can be used to actuate the jaws 16, 18. While the EAP actuator can have a variety of configurations, FIGS. 4A-5 illustrate various exemplary configurations of EAP actuators used to open and close the jaws of a surgical grasping device. As will be discussed in more detail below, the EAP actuator(s) can be configured to move the jaws from an open position to a closed position or from a closed position to an open position.

Figure 4B:
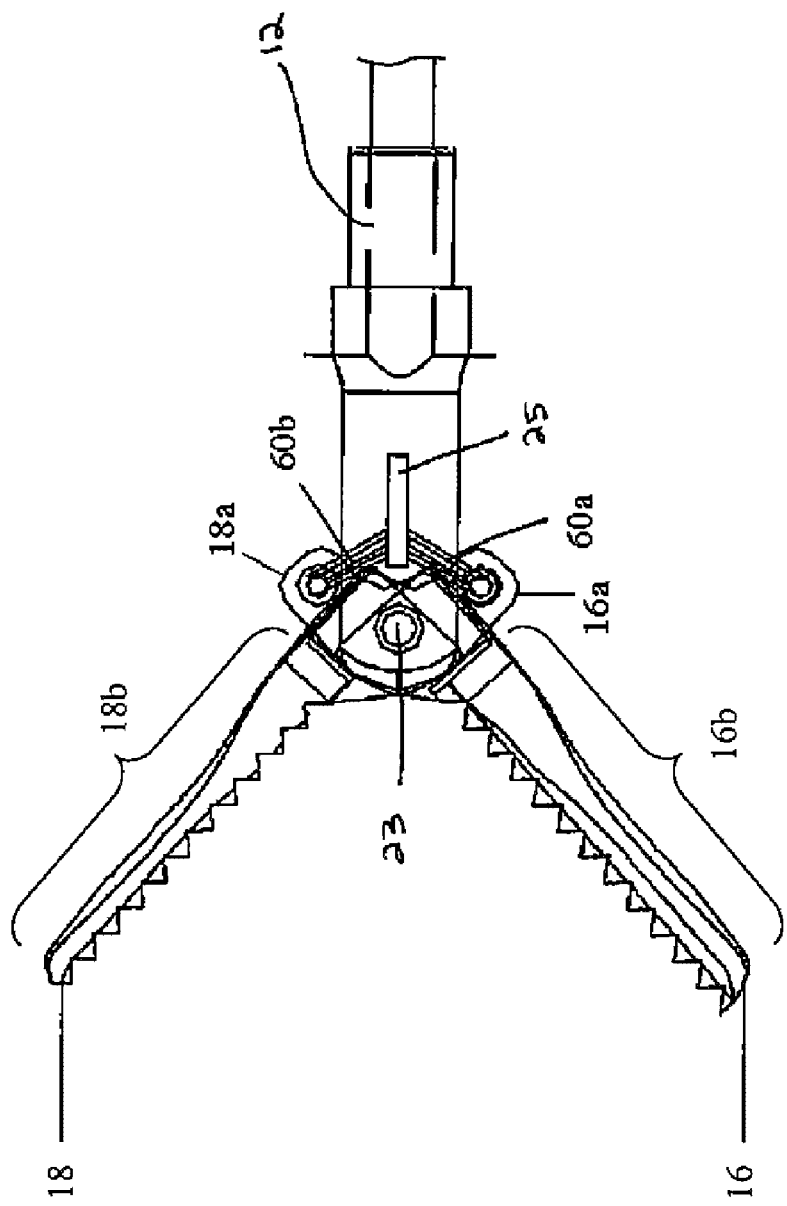
FIG. 4B is partially cross-sectional view of the end effector of FIG. 4A.
Figure 5:
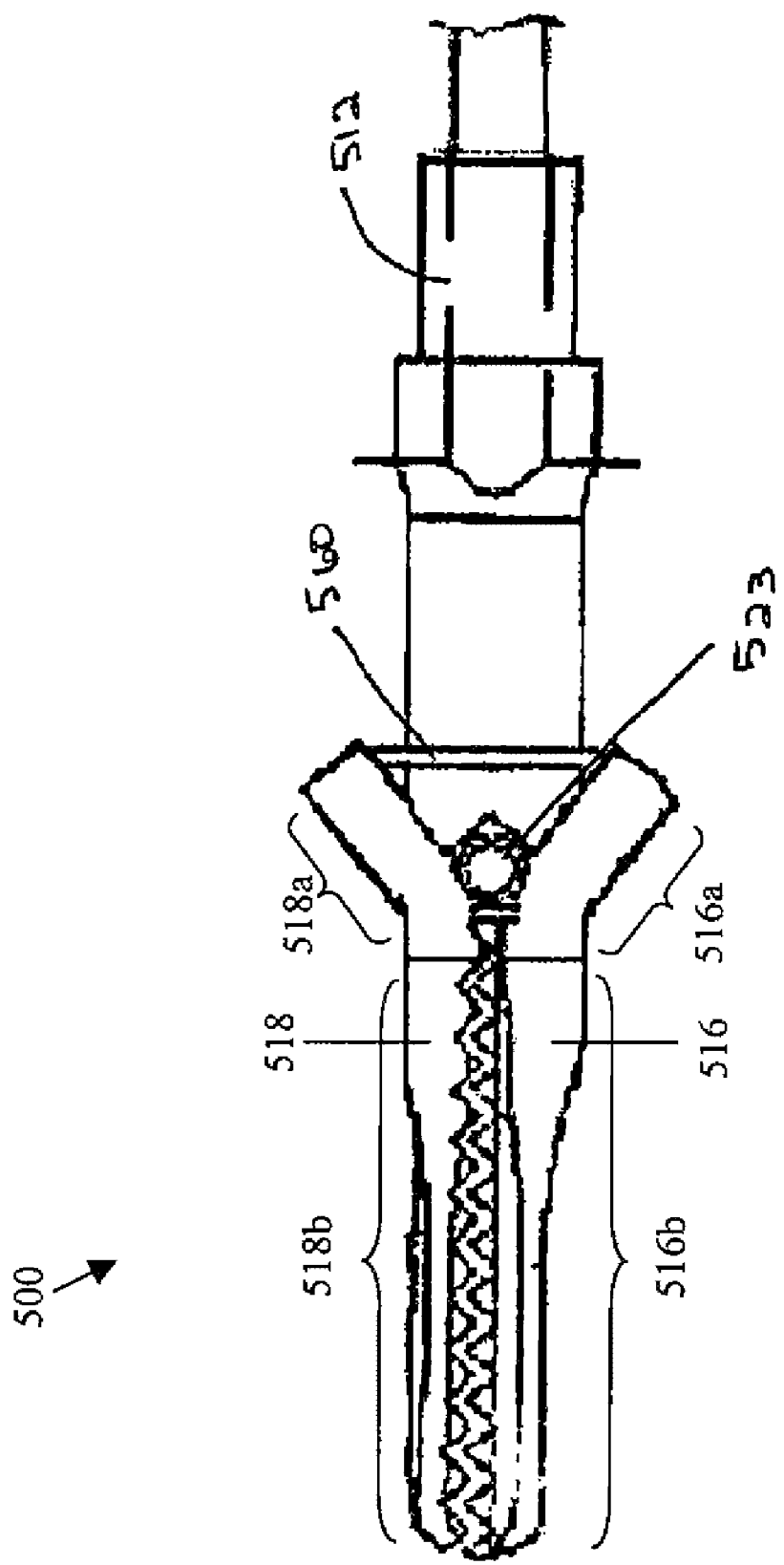
FIG. 5 is a partially cross-sectional view of another embodiment of an end effector, showing an EAP actuator for actuating the end effector.

FIGS. 4A-4B illustrate one exemplary embodiment of a technique for opening and closing first and second jaws of an end effector using EAP actuators. In this embodiment, which illustrates the end effector 11 of FIG. 3 in more detail, first and second EAP actuators 60a, 60b are used to move the jaws 16, 18 from an open position to a closed position. In general, the first and second jaws 16, 18 can be pivotally coupled to one another at a pivot point 23 formed between a proximal portion 16a, 18a and a distal portion 16b, 18b of each jaw 16, 18, i.e., the pivot point 23 is formed a distal apart from the proximal-most end of the jaws 16, 18. Such a configuration allows the EAP actuators 60a, 60b to engage and move the proximal portion 16a, 18a of the jaws 16, 18 relative to one another, thereby moving the distal portion 16b, 18b of the jaws 16, 18 about the pivot point 23. In particular, the first electroactive polymer actuator 60a extends between the proximal portion 16a of the first jaw 16 and a fixed point on the shaft 12, and the second electroactive polymer actuator 60b extends between the proximal portion 18a of the second jaw 18 and a fixed point on the shaft 12. The fixed point can be located at a variety of locations on or within the shaft 12. In the illustrated embodiment, the fixed point is in the form of a pin 25 extending through the shaft 12, as shown in FIG. 4B. A person skilled in the art will appreciate that, while two EAP actuators 60a, 60b are shown, a single EAP actuator can extend from the proximal portion 16a of the first jaw 16, around the pin 25, and attach to the proximal portion 18a of the second jaw 18. Moreover, the fixed point can be formed anywhere on, around, or within the shaft 12.

In use, energy can be selectively delivered to one or both of the first and second EAP actuators 60a, 60b through electrodes (not shown) extending through or along the shaft 12. The electrodes can couple to an energy source, such as a battery, disposed within the handle housing 14, or they can couple to an external energy source, such as an external battery or an electrical outlet. As a result of energy delivered to the actuators 60a, 60b, the actuators 60a, 60b will axially contract or shorten, pulling the proximal portions 16a, 18a of the first and second jaws 16, 18 toward the shaft 12, thereby moving the distal portions 16b, 18b of the first and second jaws 16, 18 to the closed position such that the jaws 16, 18 can grasp the an object, such as tissue, that is positioned therebetween. When energy delivery is terminated, the actuator cords 60a, 60b axially expand and return to their initial position, which allows the proximal and distal portions 16a, 18a, 16b, 18b of the jaws 16, 18 to move to the open position. While not shown, the device can also include a biasing element, such as a spring, for biasing the jaws 16, 18 to the open position. Thus, when energy delivery to the EAP actuators 60a, 60b is terminated, the biasing element will facilitate movement of the jaws 16, 18 to the open position.

FIG. 5 illustrates another exemplary embodiment of a technique for opening and closing the jaws of an end effector using EAP actuators. In this embodiment, the grasping device 500 is similar to the grasping device 400 shown in FIGS. 3-4B, however the grasping device 500 has jaws 516, 518 that are biased to the closed position and the EAP actuator is effective to move the jaws 516, 518 to the open position when energy is delivered thereto. In particular, as shown in FIG. 5, each jaw 516, 518 includes a distal engaging portion 516b, 518b and a proximal portion 516a, 518a that extends transverse to the distal portion 516b, 518b and that diverge relative to one another. An EAP actuator 560 extends between the proximal portions 516a, 518b of the first and second jaws 516, 518 at a location proximal to the pivot point 523 to allow the jaws 516, 518 to pivot about the pivot point 523 when the EAP actuator 560 is actuated.

In use, energy can be delivered to the electroactive polymer actuator 560 through electrodes extending though the shaft 512 and coupled to a power source that is disposed within or mated to the handle housing of the device. The energy will cause the electroactive polymer actuator 560 to axially contract, pulling the proximal portions 516a, 518b of the jaws 516, 518 toward one another and toward the shaft 12, thereby moving the distal portions 516b, 518b of the first and second jaws 516, 518 away from one another to an open position such that an object can be positioned between the jaws 516, 518. Termination of energy delivery will cause the electroactive polymer actuator 560 to axially expand and return to the unactuated position, which allows the proximal potions 516a, 518a of the jaws 516, 518 to move away from one another such that the distal portions 516b, 518b of the jaws 516, 518 can close. While not shown, the device can also include a biasing element, such as a spring, that can bias the jaws 16, 18 to the closed position.

Figure 13B:
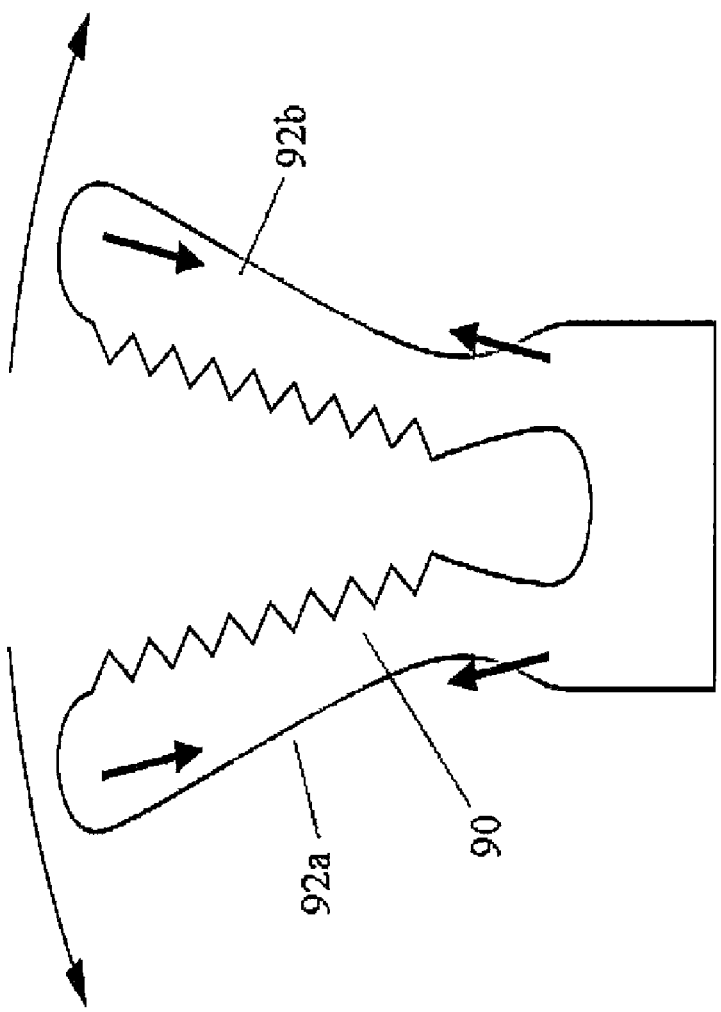
FIG. 13B is an illustration of the end effector of FIG. 13A, showing the jaws in the open position.
Figure 13A:
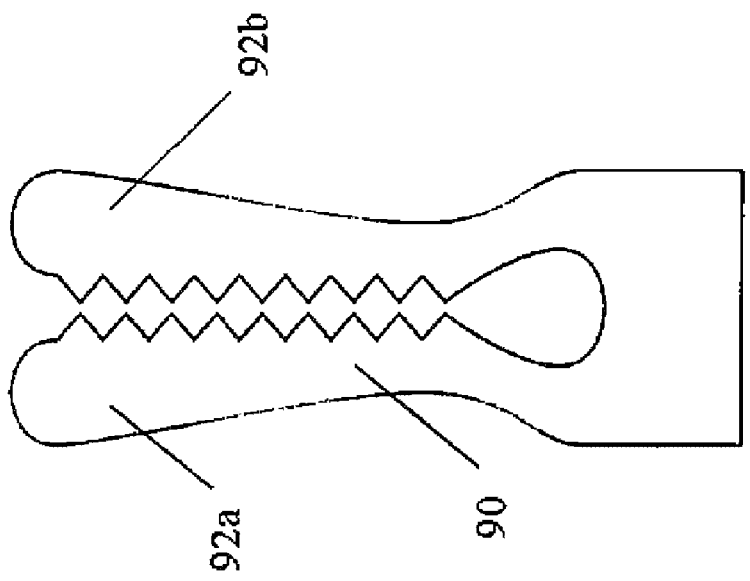
FIG. 13A is an illustration of another embodiment of an end effector having opposed jaws with first and second electroactive polymer actuators coupled thereto for moving the jaws between an open and closed position, showing the jaws in the closed position.

FIGS. 13A and 13B illustrate another embodiment of a technique for opening and closing opposed jaws of an end effector of a grasping device. In this embodiment, the jaws 90 are formed from a shape memory material such that they are biased to the closed position. First and second EAP actuators 92*a*, 92*b* extend between a proximal end of each jaw and a base of each jaw, i.e., adjacent to the pivot point of the jaws 90. The actuators 92*a*, 29*b* can extend at an angle relative to the jaws 90, i.e., the actuators 92*a*, 92*b* can diverge from one another from the base to the ends of the jaws 90. As a result, when energy is delivered to the EAP actuators 92*a*, 92*b*, the EAP actuators 92*a*, 92*b* can axially contract or shorten to apply a force to the ends of the jaws 90, thereby opening the jaws, as shown in FIG. 13B.

As noted above, the EAP actuators can have a variety of configurations. In the embodiments shown FIGS. 4A-5 each EAP actuator is in the form of a fiber-bundle type EAP actuator cord, which can be formed from a single EAP fiber strand, or multiple EAP fibers woven or braided together to form a cord. In other embodiments, each EAP actuator can be in the form of a laminate or composite EAP. A person skilled in the art will appreciate the variety of actuator configurations that can be used to effect movement of the first and second jaws.

Articulation

As previously indicated, the present invention also provides exemplary methods and devices for articulating an end effector (i.e., opposed jaws) of a grasper. FIGS. 6A-12B illustrate various exemplary embodiments of articulation joints and electroactive polymer actuators for effecting articulation. These articulation joints can be incorporated into any grasper, including those exemplary prior art instruments described above.

Figure 6A:
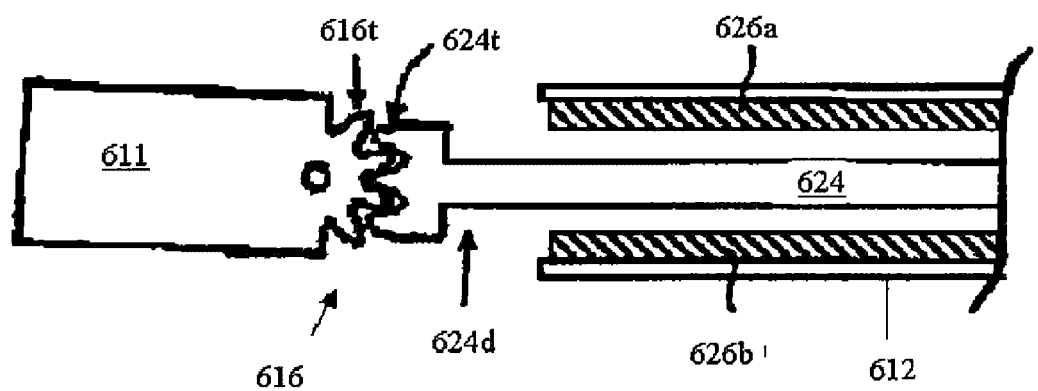
FIG. 6A is a cross-sectional view of a distal portion one exemplary embodiment of a grasping device, showing EAP actuators in a non-actuated configuration for effecting articulation of the end effector.
Figure 6B:
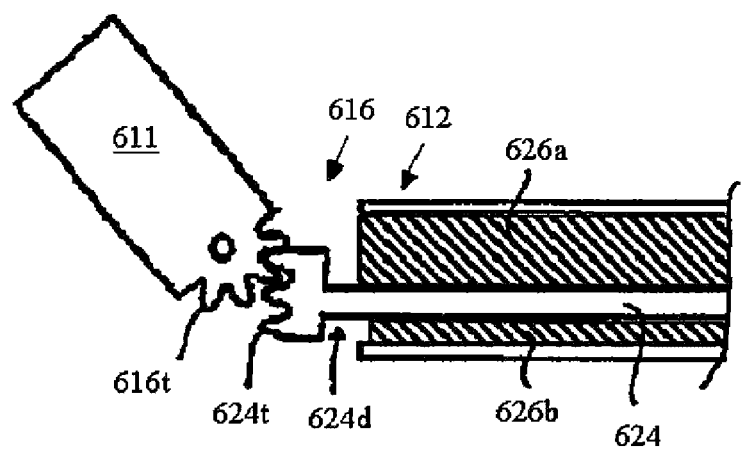
FIG. 6B is a cross-sectional view of the distal portion of the grasping device shown in FIG. 6A, showing one of the EAP actuators electrically actuated to articulate the end effector.

Referring first to FIGS. 6A-6B, a distal end 612*b* of the elongate shaft 612 is shown coupled to a proximal end of the end effector 611 by a pivot joint 616, such that the end effector 611 can pivot relative to the shaft 612 about the pivot joint 616. The device also includes a slide bar 624 extending through the elongate shaft 612 and having a distal end 624*d* with gear teeth 624*t* formed thereon and adapted to engage corresponding gear teeth 616*t* formed on the end effector 611. The device can also include one or more electrically expandable and contractible actuators, such as an EAP actuator, for moving the slide bar 624 to cause the gear teeth 624*t* on the slide bar 624 to move the gear teeth 624*t* on the end effector 611 and thereby pivot the end effector 611 relative to the elongate shaft 612. While the EAP actuator(s) can effect movement of the slide bar 624 using a variety of techniques, in one exemplary embodiment the EAP actuators are configured to move the slide bar 624 laterally. In particular, a first EAP actuator 626*a* can extend through at least a portion of the elongate shaft 612 adjacent to a first lateral side of the slide bar 624, and a second EAP actuator 626*b* can extend through at least a portion of the elongate shaft 612 adjacent to a second, opposed lateral side of the slide bar 624, as shown in FIGS. 6A-6B. Either type of EAP actuator can be used, but in an exemplary embodiment the EAP actuators 626*a*, 626*b* are laminate type EAP actuators that are adapted to expand laterally when energy is delivered thereto. FIG. 6A illustrates both actuators 626*a*, 626*b* in a non-expanded, un-actuated configuration, where no energy is delivered to either actuator 626*a*, 626*b*. FIG. 6B illustrates the first EAP actuator 626*a* laterally expanded to move the slide bar 624 laterally toward the second EAP actuator 626*b*, thereby causing the slide bar 624 to pivot the end effector 611 in a direction opposite to the direction of movement of the slide bar 624. Energy can be delivered to the actuators 626*a*, 626*b* through electrodes extending through the shaft 612 and coupled to an energy source disposed within or coupled to a handle of the device, e.g., a battery source or an electrical outlet or other energy source. The handle can also include a control mechanism, such as a sliding lever, rotatable knob, or dial, coupled thereto and adapted to control the amount of energy delivered to each actuator 626*a*, 626*b*. The amount of energy delivered to each actuator 626*a*, 626*b* is determinative of the amount of expansion of the actuators 626*a*, 626*b*, thus allowing the amount of pivotal movement of the end effector 611 to be selectively adjusted.

A person skilled in the art will appreciate that, while FIGS. 6A-6B illustrate a laterally-moving slide bar 624 with laterally expanding EAP actuators 626*a*, 626*b*, the slide bar 624 and actuators 626*a*, 626*b* can have a variety of other configurations. For example, multiple EAP actuators in the form fiber bundles can extend laterally between an inner surface of the elongate shaft 612 and the slide bar 624. When energy is delivered to the actuators, the actuators can contract or shorten in length to pull the slide bar 624 toward the elongate shaft 612, thereby moving the slide bar 624 laterally. Alternatively, the slide bar 624 can be configured to move longitudinally to effect movement of the end effector 611, and the EAP actuator can be used to effect longitudinal movement of the slide bar 624. In other embodiments, the slide bar itself, or at least a portion of the slide bar, can be formed from an EAP actuator that is adapted to expand axially in a desired direction to move the slide bar laterally.

Figure 7A:
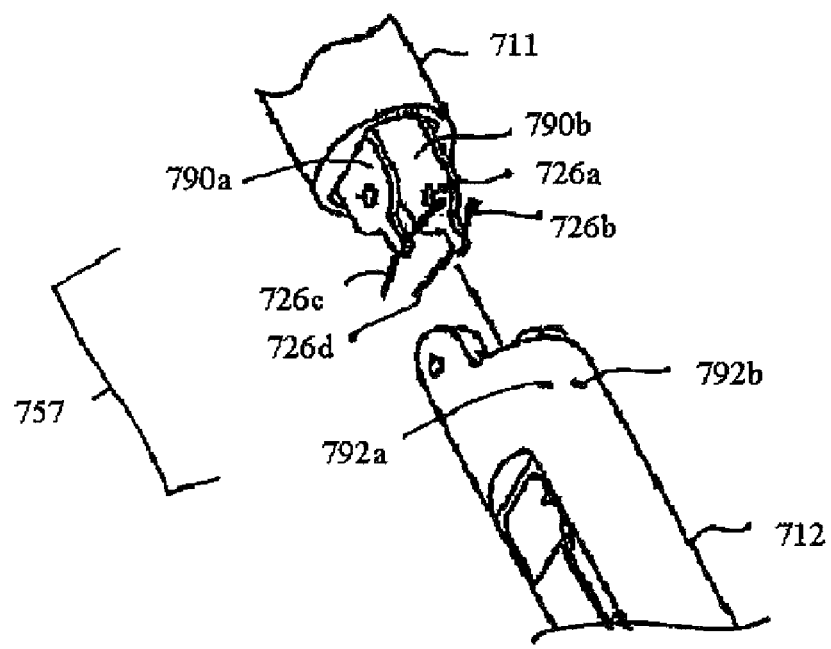
FIG. 7A is an exploded perspective view of another embodiment of an end effector movably coupled to a distal portion of a shaft and having EAP actuators for articulating the end effector.
Figure 7B:
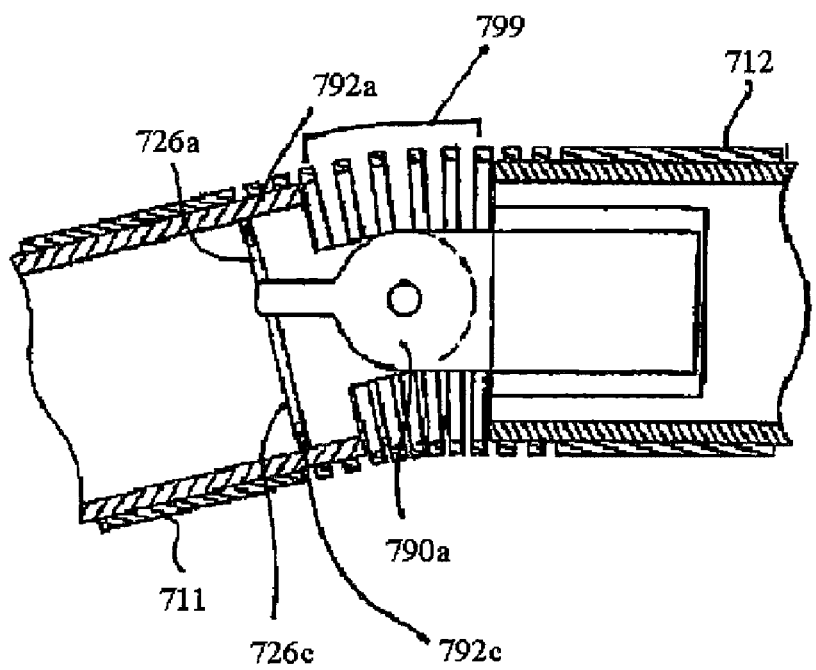
FIG. 7B is a partially cross-sectional view of the end effector of the grasping device and shaft shown in FIG. 7A, showing one of the EAP actuators electrically actuated to articulate the end effector.

FIGS. 7A-7B illustrate another embodiment of a technique for articulating an end effector of a surgical grasper device. In this embodiment, the end effector 711 is pivotally coupled to the elongate shaft 712 by first and second opposed arms 790*a*, 790*b* coupled to opposed sides of the elongate shaft 712. First and third EAP actuators 726*a*, 726*c* are attached to and extend from opposed sides of a terminal end of the first arm 790*a*, and second and fourth EAP actuators 726*b*, 726*d* are attached to and extend from opposed sides of a terminal end of the second arm 790*b*. The distal end of each EAP actuator 726*a*-*d* is coupled to an inner sidewall of the elongate shaft 712 at an attachment point (first, second, and third attachment points 792*a*, 792*b*, 792*c* are shown). As a result, the first and second actuators 726*a* and 726*b* are attached to one side of the elongate shaft 712, and the third and fourth actuators 726*c* and 726*d* are attached to an opposite side of the elongate shaft 712. In use, energy can be delivered to the first and second EAP actuators 726*a*, 726*b* to cause the actuators 726*a*, 726*b* to axially contract or shorten, thereby pulling the first and second arms 790*a*, 790*b* in a lateral direction towards the first and second attachment points 792*a*, 792*b*. As a result, the end effector 711 is pivoted in a first direction. When energy delivery is terminated, the first and second actuators 726*a*, 726*b* will axially expand returning to their initial configuration, thereby moving the end effector 711 to its initial position in which it is longitudinally aligned with the elongate shaft 712. Energy can be delivered to the third and fourth actuators 726*c*, 726*d* to similarly move the end effector 711 in an opposite direction. As previously discussed, the amount of energy delivered can be controlled to control the amount of pivotal movement of the end effector 711. As shown in FIG. 7B, the device can also include a covering 799 surrounding at least a portion of the pivot frame assembly 757 to provide support thereto.

Figure 8:
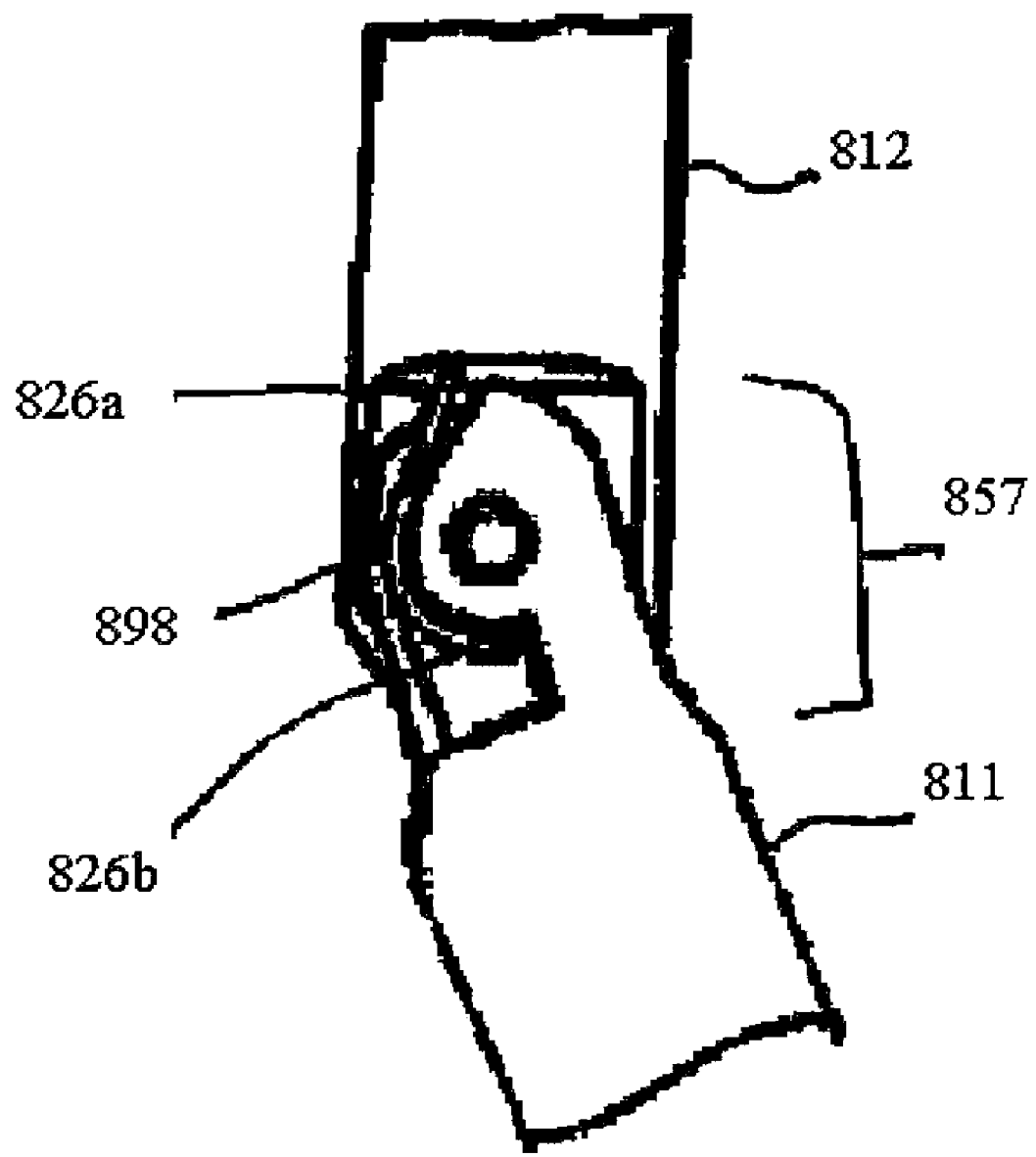
FIG. 8 is a partially cross-sectional view of another embodiment of an end effector movably coupled to a distal portion of a shaft and having EAP actuators for articulating the end effector.

FIG. 8 illustrates yet another embodiment of a technique for articulating an end effector of a surgical grasper device. In this embodiment, one or more actuating members can be incorporated into a pulley 898 that is part of a pivoting frame assembly 857. The pulley 898 can be made entirely of EAP actuators or, alternatively, EAP actuators can be attached to proximal and distal ends of the pulley 898. In the illustrated embodiment, first and second EAP actuators 826a, 826b are attached to the proximal and distal ends of the pulley 898. The EAP actuators 826a, 826b are anchored to the elongate shaft 812 to push and pull the end effector 811 to effect articulation. In particular, energy delivery to one of the EAP actuators, e.g., the first EAP actuator 826a, causes the first EAP actuator 826a to axially contract or shorten to move the pulley 898 in a first direction, thereby causing the end effector 811 to pivot in a first direction. Conversely, energy delivery to the second EAP actuator 826b causes the second EAP actuator to axially contract or shorten to move the pulley 898 in a second, opposite direction, thereby causing the end effector 811 to pivot in a second, opposite direction. Again, energy delivery can be controlled to control the amount of movement of the end effector 811.

Figure 9A:
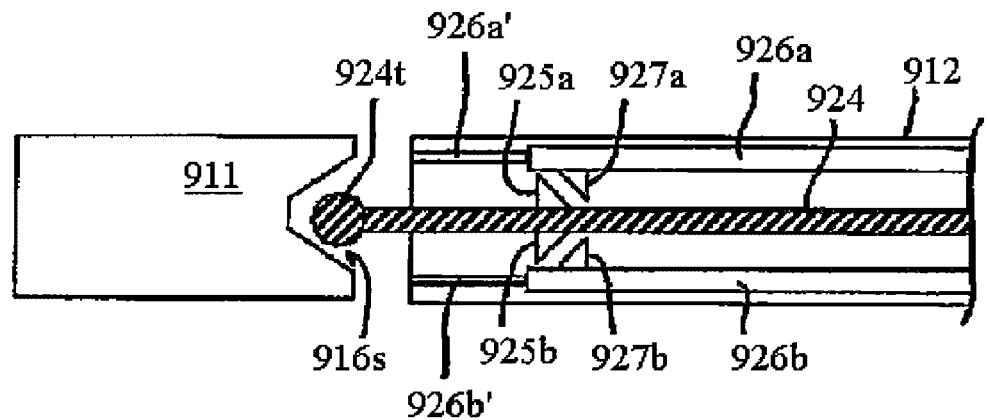
FIG. 9A is a partially cross-sectional view of another embodiment of an end effector movably coupled to a distal portion of a shaft and having EAP actuators for articulating the end effector.
Figure 9B:
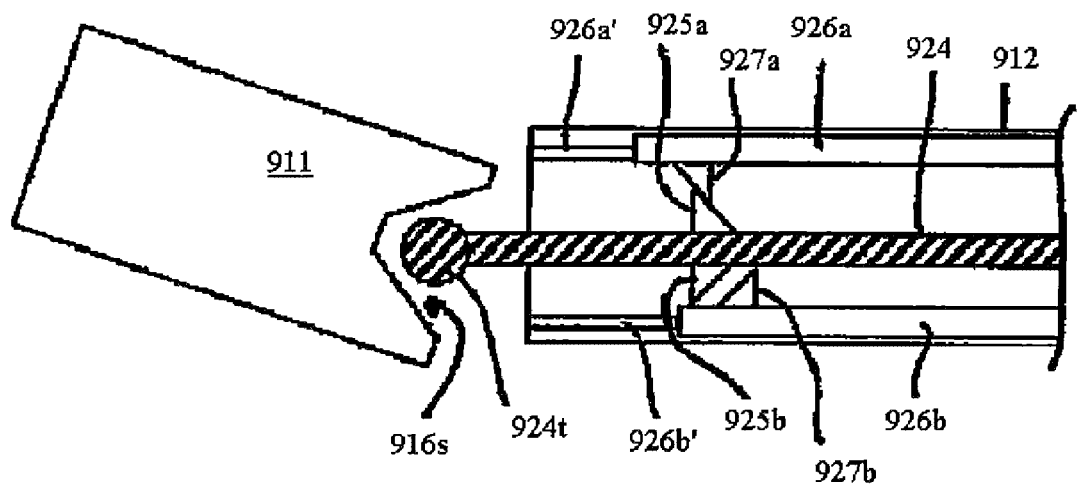
FIG. 9B is a partially cross-sectional view of the end effector and shaft shown in FIG. 9A, showing one of the EAP actuators electrically actuated to articulate the end effector.

FIGS. 9A-9B illustrate another embodiment of a technique for articulating an end effector relative to an elongate shaft of a grasper. In this embodiment, the elongate shaft 912 includes a slide bar 924 extending therethrough and having a ball 924t formed on a distal end thereof and received within a corresponding socket 916s formed in a proximal end of the end effector 911. The slide bar 924 also includes cam surfaces 925a, 925b formed thereon, preferably at a location proximal to the distal end of the elongate shaft 912. The cam surfaces 925a, 925b can have a variety of shapes and sizes, but in an exemplary embodiment, as shown, the cam surfaces 925a, 925b extend outward from opposed sides of the slide bar 924 and they are wedge-shaped members that increase in width in a proximal-to-distal direction. The device also includes first and second actuating members 926a, 926b extending through the elongate shaft 912 and positioned on opposed sides of the slide bar 924. Each actuating member 926a, 926b includes a cam surface 927a, 927b formed thereon and adapted to abut against the cam surfaces 925a, 925b formed on the slide bar 924. As a result, distal movement of the first actuating member 926a will cause the cam surface 927a formed thereon to slide against the cam surface 925a formed on the slide bar 924, thereby moving the slide bar 924 laterally away from the first actuating member 926a. As a result of the lateral movement of the slide bar 924, the ball 924t will cause the end effector 911 to pivot relative to the elongate shaft 912. Conversely, distal movement of the second actuating member 926b will cause the cam surface 927b formed thereon to slide against the cam surface 925b formed on the slide bar 924, thereby moving the slide bar 924 laterally away from the second actuating member 926b, and thus pivoting the end effector 911 in an opposite direction. A biasing element (not shown), such as a spring, can be disposed on each side of the slide bar 924 to bias the slide bar 924 to the central, resting position shown in FIG. 9A, thereby allowing the slide bar 924 to return to the resting position when the actuating members 926a, 926b are moving proximally.

In an exemplary embodiment, movement of each actuating member 926a, 926b can be achieved using an EAP actuator coupled thereto. As shown in FIGS. 9A and 9B, an EAP actuator cord 926a', 926b', preferably in the form of a fiber bundle type actuator, extends between a distal end of each actuating member 926a, 926b and a distal end of the shaft 912. When energy is selectively delivered to one of the EAP actuating cords, e.g., the first actuating cord 926a', the cord 926a' will axially contract or shorten, as shown in FIG. 9B, thereby pulling the actuating member 926a coupled to the actuated EAP cord 926a' in a distal direction. The cam surface 927a on the actuating member 926a will abut against the cam surface 925a on the slide bar 924 to move the slide bar 924 laterally toward the second actuating member 926b. As a result, the ball 924t on the distal end of the slide bar 924 will cause the end effector 911 to articulate or pivot thereabout.

A person skilled in the art will appreciate that the EAP actuators can have a variety of other configurations, and they can effect movement of the slide bar using a variety of other techniques. For example, rather than pulling the slide bar 924 distally when energy is delivered to the EAP actuating cords 926a', 926b', the EAP actuators can be coupled to a proximal end of the slide bar 924 and they can be adapted to push the slide bar 924 distally. In other embodiments, the cam surface 927a, 927b formed on each actuating member 926a, 926b can be formed from an EAP actuator such that energy delivery to the cam surface 927a, 927b causes the cam surface 927a, 927b to expand toward the slide bar 924, thereby moving the slide bar 924 in a desired direction to articulate the end effector 911. The amount of movement of each actuating member 926a, 926b, and thus the amount of articulation of the end effector, can also be controlled by controlling the amount of energy delivered to each EAP actuator.

Figure 10A:
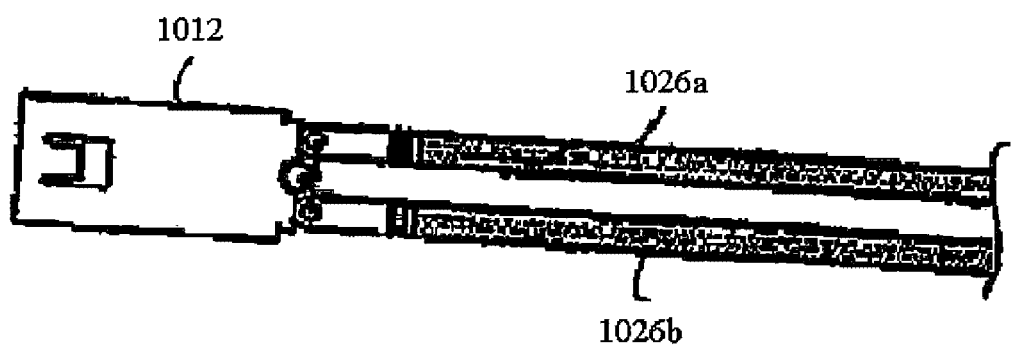
FIG. 10A is a partially cross-sectional view of yet another embodiment of an end effector movably coupled to a distal portion of a shaft and having EAP actuators for articulating the end effector.
Figure 10B:
FIG. 10B is a partially cross-sectional view of the end effector and shaft shown in FIG. 10A, showing one of the EAP actuators electrically actuated to articulate the end effector.

FIGS. 10A-10B illustrate yet another embodiment of a technique for articulating an end effector 1012 of a grasper. In this embodiment, rather than using a slide bar to pivot the end effector 1012, two actuating members 1026a, 1026b are coupled directly to opposed sides of the end effector 1012 to push and pull the end effector 1012 to effect articulation. In particular, a distal end of each actuating member 1026a, 1026b is coupled to a proximal end of the end effector 1012 by a pivot joint, such that proximal movement of the first actuating member 1026a causes the end effector 1012 to pivot about the second actuating member 1026b, and proximal movement of the second actuating member 1026b causes the end effector 1012 to pivot about the first actuating member 1026a. The actuating members 1026a, 1026b can be moved using a variety of techniques. For example, all or a portion of each actuating member 1026a, 1026b can be formed from an EAP that is adapted to axially expand, or the actuating members 1026a, 1026b can be coupled to an EAP actuator for moving the actuating members 1026a, 1026b proximally and distally to articulate the end effector 1012.

Figure 11:
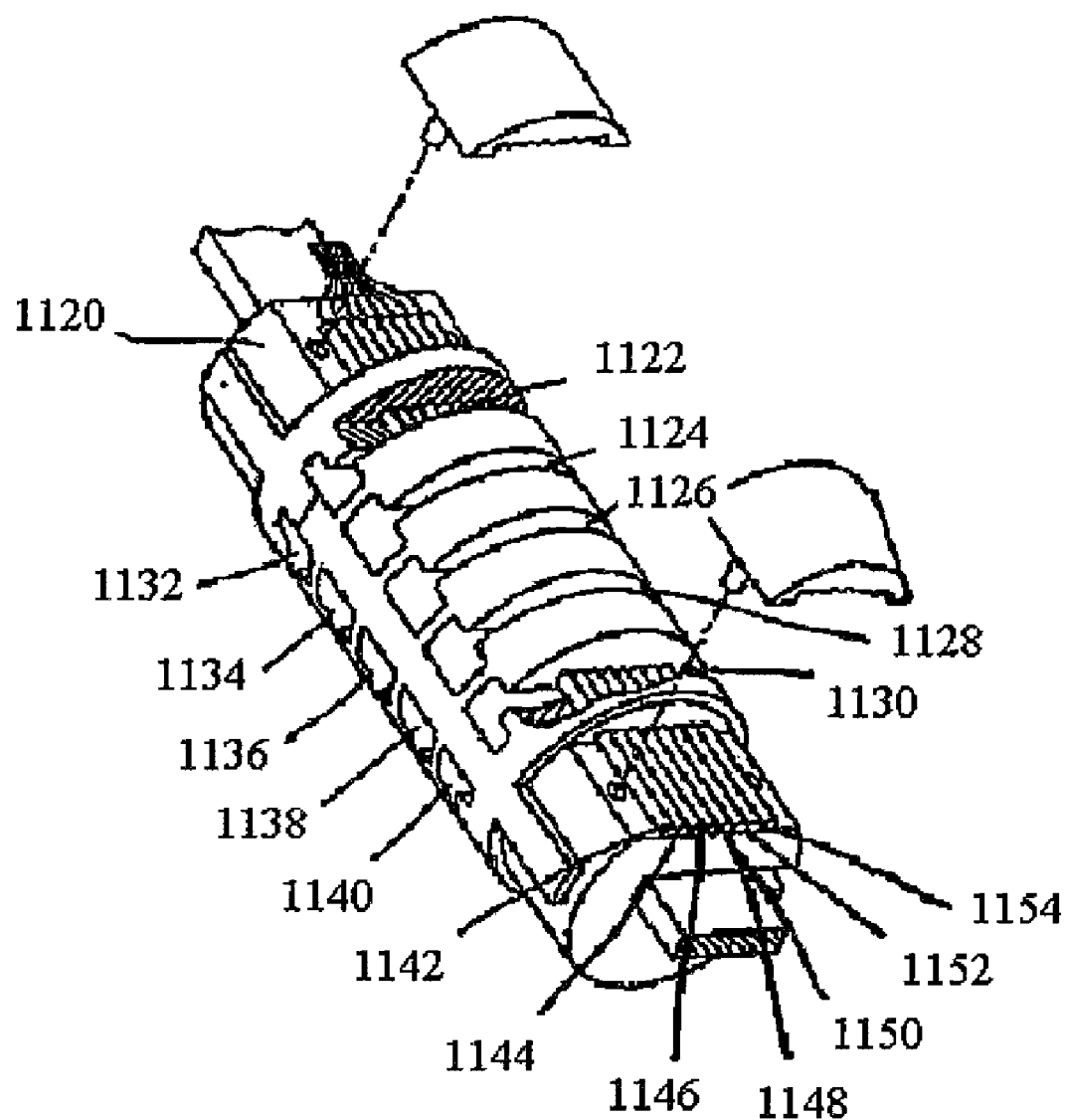
FIG. 11 is a perspective view of yet another embodiment of an end effector movably coupled by a flexible portion to a shaft and having EAP actuators for articulating the end effector.

FIG. 11 illustrates another embodiment of a technique for articulating an end effector of a grasper device. In this embodiment, the elongate shaft 1120 includes a flexible portion formed by a plurality of cut out portions 1122, 1124, 1126, 1128, 1130, 1132, 1134, 1136, 1138, 1140, 1142 (hereinafter 1122-1142) formed on opposed sides of the elongate shaft 1120. The cut out portions allow the elongate shaft 1120 to flex thereabout. One or more actuators can be positioned relative to the cut out portions to effect pivotal or bending movement of an end effector (not shown) relative to the elongate shaft 1120. FIG. 11 illustrates multiple EAP actuator cords 1144, 1146, 1148, 1150, 1152, 1154 (hereinafter 1144-1154) extending longitudinally through the elongate shaft 1120 where the cut out portions are formed. The EAP actuator cords 1144-1154 extend longitudinally parallel to one another, and they are coupled to the elongate shaft 1120 at a first end just proximal to the cut out portions 1122-1142 and at a second end just distal to the cut out portions 1122-1142. In use, energy can be selectively delivered to any one or combination of the EAP actuator cords 1144-1154 to flex the cut out portions 1122-1142 and thereby articulate the end effector in a desired direction. For example, energy can be delivered to the first EAP actuator cord 1144 to cause the first actuator cord 1144 to axially contract or shorten, thereby pulling the opposed ends of the cord 1144 toward one another.

Since the ends of the first actuator cord 1144 are attached to the elongate shaft 1120 at opposed ends of the cut out portions, and since the first EAP actuator cord 1144 is offset from a central axis of the elongate shaft 1120, the first EAP actuator cord 1144 will cause the elongate shaft 1120 to bend in a first direction. Accordingly, one or more actuator cords 1144-1154 can be selectively activated, i.e., energy can be selectively delivered thereto, to effect movement of the end effector in a desired direction. A person skilled in the art will appreciate that a variety of other techniques can be used to cause the cut out portions to bend.

In other embodiments, one or more EAP actuators can be positioned within, on, or around the flexible portion of the elongate shaft at various locations, and the EAP actuators can be configured to flex the flexible portion when energy is delivered to the actuators, thereby articulating the end effector. For example, multiple EAP actuators can extend axially along distinct portions of a flexible portion of an elongate shaft, or they can be positioned at various other locations around the circumference of the flexible portion. In use, energy delivery to a first actuator, for example, to cause the first actuator to axially contract thereby bending a portion of the flexible portion. A user can thus selectively deliver energy to one or more actuators to articulate and position the end effector as desired.

A person skilled in the art will appreciate that any of the above embodiments can include a locking feature that allows the device to maintain its articulated position when energy delivery is terminated to the EAP actuators. In particular, when energy delivery is terminated the EAP actuator(s) axially expands to return the end effector to its initial position in which it is longitudinally aligned with the elongate shaft. A locking mechanism can thus be used to lock the end effector in a desired articulated position prior to terminating energy delivery to the EAP actuators.

Figure 12A:
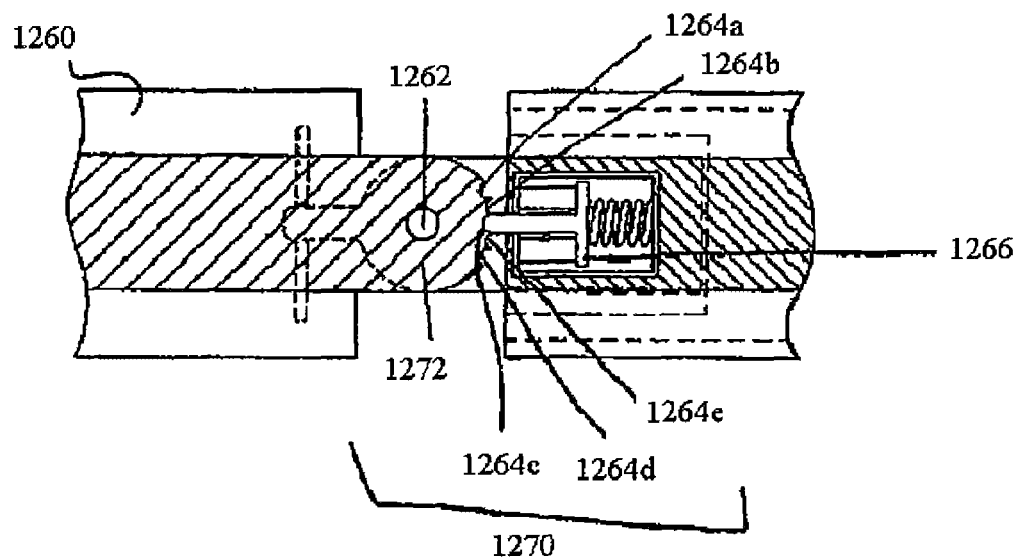
FIG. 12A is a perspective view of one exemplary embodiment of a locking mechanism in an unactivated position for locking a movable joint between an end effector and a shaft in any of FIGS. 6A-11.
Figure 12B:
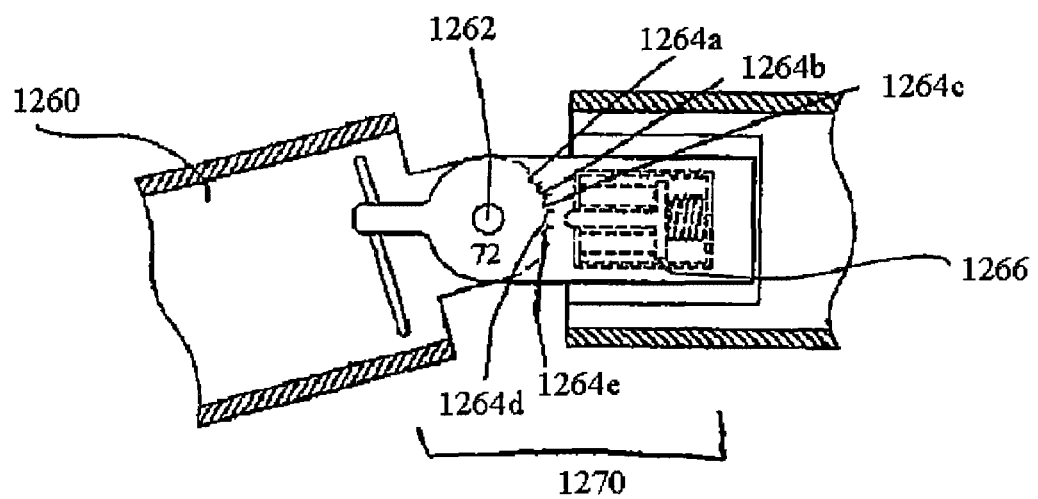
FIG. 12B is a perspective view of the locking mechanism of FIG. 12A activated to lock the movable joint in a fixed position.

While the locking mechanism can have a variety of configurations, FIGS. 12A-12B illustrate one exemplary embodiment of an articulation lock 1270 that is incorporated into a pivoting articulation joint 1262. As shown, the articulation joint 1262 includes a rotary structure 1272 having a plurality of holes 1264a, 1264b, 1264c, 1264d, 1264e that are adapted to receive a plunger to prevent rotational movement of the articulation joint 1262. A stop, which in one embodiment can be a spring loaded plunger 1266, is formed within the elongate shaft of the device and located proximal to the rotary structure 1272. The plunger 1266 is also coupled to an EAP actuator (not shown) that, when actuated with energy, effects movement of the plunger 1266 thereby allowing the articulation joint 1262 to move. In particular, as shown in FIG. 12A, when the device is in an un-actuated position, the plunger 66 rests in one of the holes (hole 64e as shown) of the rotary structure 1272, thereby maintaining the end effector in a fixed position. Energy delivery to the EAP actuator, as shown in FIG. 12B, will pull the plunger 1266 out of the hole 1264e to allow the articulation joint 1262 to move to a desired position. The various techniques previously described can be used to articulate the end effector. Once the end effector is moved to a desired articulated position, the EAP actuator can be de-actuated, i.e., energy delivery can be terminated, allowing the spring to bias the plunger 1266 into one of the holes of the rotary structure 1272. The end effector is thereby again maintained in a fixed position. One skilled in the art will appreciate that a variety of other locking mechanism can be incorporated into an articulating joints, such as a ratchet and teeth system.

A person skilled in the art will appreciate that the EAP actuators can have a variety of other configurations to effective movement of the plunger. For example, in another embodiment an EAP actuator can replace the plunger and can be directly connected to a driver to move the driver distally through the elongate shaft. One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A grasping device, comprising:
   a shaft having opposed first and second jaws formed on a distal end thereof and movable between a closed position and an open position in which the first and second jaws can receive an object therebetween; and
   at least one electroactive polymer actuator having a first terminal end coupled to the first jaw and a second terminal end coupled to one of the distal end of the shaft and the second jaw, the at least one electroactive polymer actuator effective to move the first and second jaws relative to each other between the open and closed positions.

2. The device of claim 1, wherein the at least one electroactive polymer actuator is configured to move the first and second jaws to the open position when energy is delivered thereto.

3. The device of claim 1, wherein the at least one electroactive polymer actuator is configured to move the first and second jaws to the closed position when energy is delivered thereto.

4. The device of claim 1, wherein the first and second jaws are coupled to one another at a pivot point formed between a proximal end and a distal end of each jaw, and wherein the at least one electroactive polymer actuator is coupled to each jaw at a location proximal to the pivot point.

5. The device of claim 4, wherein the at least one electroactive polymer actuator comprises a first electroactive polymer actuator extending between the proximal end of the first jaw and the shaft, and a second electroactive polymer actuator extending between the proximal end of the second jaw and the shaft.

6. The device of claim 5, wherein the first and second electroactive polymer actuators are adapted to axially contract when energy is delivered thereto to pull the proximal ends of the first and second jaws toward the shaft.

7. The device of claim 6, wherein the jaws are adapted to move from the open position to the closed position when energy is delivered to the first and second electroactive polymer actuators.

8. The device of claim 6, wherein the jaws are adapted to move from the closed position to the open position when energy is delivered to the first and second electroactive polymer actuators.

9. The device of claim 4, wherein the at least one electroactive polymer actuator is coupled to and extends between the proximal end of each jaw.

10. The device of claim 1, wherein the first and second jaws are biased to an open position, and the at least one electroactive polymer actuator is adapted to move the jaws to a closed position when energy is delivered thereto.

11. The device of claim 1, wherein the first and second jaws are biased to a closed position, and the at least one electroactive polymer actuator is adapted to move the jaws to an open position when energy is delivered thereto.

12. The device of claim 1, further comprising a handle formed on the proximal end of the shaft and including a control mechanism adapted to selectively deliver energy to the at least one electroactive polymer actuator.

13. The device of claim 1, further comprising an articulation joint formed on the shaft and adapted to allow the first and second jaws to articulate relative to a longitudinal axis of the shaft.

14. The device of claim 13, further comprising at least one electroactive polymer actuator coupled to the articulation joint and adapted to articulate the first and second jaws when energy is delivered to the at least one electroactive polymer actuator.

15. The device of claim 1, wherein the at least one electroactive polymer actuator is configured to expand when energy is applied thereto in a direction orthogonal to a longitudinal axis of the shaft to move the first and second jaws between the open and closed positions.

16. The device of claim 15, wherein opposed ends of the at least one electroactive polymer actuator are coupled to proximal portions of the first and second jaws.

17. The device of claim 15, wherein the at least one electroactive polymer actuator contracts in a direction orthogonal to the longitudinal axis of the shaft when energy is applied thereto to move the jaws to an open position.

18. The device of claim 1, further comprising a second electroactive polymer actuator disposed within the shaft and configured to expand in a direction orthogonal to a longitudinal axis of the shaft when energy is applied thereto to articulate the jaws relative to the shaft.

19. The device of claim 18, wherein expansion of the second electroactive polymer actuator is configured to move a slide bar in communication with the jaws and disposed within the shaft orthogonally relative to the longitudinal axis of the shaft to thereby articulate the jaws relative to the shaft.

20. A grasping device, comprising:
a shaft having an end effector with opposed jaws formed thereon and pivotally movable relative to one another, the shaft having an electrical cable extending therethrough; and
at least one electroactive polymer actuator coupled to the end effector and effective to pivot the opposed jaws relative to each other when energy is delivered to the at least one electroactive polymer actuator through the electrical cable.

21. The device of claim 20, wherein the opposed jaws are biased to an open position, and wherein the at least one electroactive polymer actuator is effective to move the opposed jaws to a closed position when energy is delivered to the at least one electroactive polymer actuator.

22. The device of claim 20, wherein the opposed jaws are biased to a closed position, and wherein the at least one electroactive polymer actuator is effective to move the opposed jaws to an open position when energy is delivered to the at least one electroactive polymer actuator.

23. The device of claim 20, wherein the at least one electroactive polymer actuator comprises a first electroactive polymer actuator coupled to and extending between a proximal end of one of the opposed jaws and the shaft, and a second electroactive polymer actuator coupled to and extending between a proximal end of the other one of the opposed jaws and the shaft.

24. The device of claim 20, wherein an electroactive polymer actuator extends between a proximal end of each of the opposed jaws.

* * * * *